United States Patent [19]

Yamato et al.

[11] Patent Number: 4,866,047
[45] Date of Patent: Sep. 12, 1989

[54] METHOD FOR INHIBITING THE FORMATION OF URINARY CALCULUS UTILIZING 24,25-(OH)$_2$-D$_3$

[75] Inventors: Hideyuki Yamato, Tokyo; Yuji Maeda, Nagareyama; Takayoshi Fujii, Tokyo; Yasuhiko Kobayashi, Niiza; Kenichi Saito, Tokyo; Fumio Hirose, Tokyo; Tadaaki Kato, Tokyo; Chikao Yoshikumi, Tokyo, all of Japan

[73] Assignee: Kureha Kagaku Kogyo Kabushiki Kaisha, Tokyo, Japan

[21] Appl. No.: 103,788

[22] Filed: Oct. 1, 1987

[30] Foreign Application Priority Data

Oct. 3, 1986 [JP] Japan .................................. 61-235824

[51] Int. Cl.$^4$ ............................................. A61K 31/59
[52] U.S. Cl. ..................................... 514/167; 514/891
[58] Field of Search ................................. 514/167, 891

[56] References Cited

U.S. PATENT DOCUMENTS 3,715,374  2/1973  DeLuca et al. .
3,994,878  11/1976  Partridge, Jr. et al. .
4,012,509  3/1977  Frank .
4,364,941  12/1982  Kiyoki et al. .
4,442,093  4/1982  Maeda et al. ........................ 514/167
4,501,738  2/1985  Yamato et al. .
4,590,184  5/1986  Maeda et al. .

FOREIGN PATENT DOCUMENTS 0086476  12/1986  European Pat. Off. .
1129130  6/1986  Japan .................................. 514/167
1130225  6/1986  Japan .................................. 514/167

OTHER PUBLICATIONS

A. E. Caldas, et al., J. Lab. Clin. Med., vol. 91, No. 5, 1978, pp. 840–849.
J. C. Netelenbos, et al., Arch. Intern. Med., vol. 145, 4/85, pp. 681–684.
M. Gascon-Barre, et al., Ann. Nutr. Metab., vol. 29, 1985, pp. 289–296.

Primary Examiner—Douglas W. Robinson
Assistant Examiner—Joseph A. Lipovsky
Attorney, Agent, or Firm—David G. Conlin; Ronald I. Eisenstein

[57] ABSTRACT

Disclosed herein is a method for inhibiting the formation of urinary calculus by the administration of 24,25-dihydroxycholecarciferol.

8 Claims, No Drawings

METHOD FOR INHIBITING THE FORMATION OF URINARY CALCULUS UTILIZING 24,25-(OH)$_2$-D$_3$

BACKGROUND OF THE INVENTION

The present invention relates to a method for inhibiting the formation of urinary calculus, which comprises administering 24,25-dihydroxycholecarciferol.

The formation of urinary calculus is a disease of a high frequency among the diseases of urinary system. The words "urinary calculus" herein mentioned includes renal calculus, prostatic calculus, renal pelvic calculus, ureteric calculus, vesical calculus and urethral culculus.

Although the above disease is treated, at present in many cases, by the operative extirpation of the calculus, there have been the defects of giving pain to the patient in the operation and hospitalization is required.

Recently, the establishment of the internal medical method for treating urinary calculus, has been regarded as the very important problem, and the development of a prophylactic for urinary calculus has been expected along with the development of the therapeutic medicine.

As a result of the present inventors' studies on the pharmacological effects of various substances, which exist in a healthy human body and have the verified safety, to the urinary calculus, it has been found that 24,25-dihydroxycholecarciferol (hereinafter referred to as the present substance or 24,25-(OH)$_2$—D$_3$) remarkably inhibits the formation of urinary calculus in the experiment using model animals, and on the basis of the finding, the present invention have been accomplished.

SUMMARY OF THE INVENTION

In a first aspect of the present invention, there is provided a method for inhibiting the formation of urinary calculus, which comprises administering an effective dosage amount of 24,25-(OH)$_2$—D$_3$.

In a second aspect of the present invention, there is provided a method for prophylaxis of urinary calculosis (urinary lithiasis), which comprises administering an effective dosage amount of 24,25-(OH)$_2$—D$_3$.

DETAILED DESCRIPTION OF THE INVENTION

Every one of the present substances has been known and for instance, the present substances have been disclosed in Pharmacia, 10, 319 –322(1974).

The resent substance includes 24R,25- (OH)$_2$—D$_3$, 24S, 25-(OH)$_2$—D$_3$ or a mixture thereof, and in particular, it is preferable to use 24R,25-(OH)$_2$—D$_3$ as the present substance.

In the present invention, although 24,25-(OH)$_2$—D$_3$ may be preferably administered parenterally, it may also be administered orally.

The pharmaceutical preparation containing the present substance as a pharmaceutical active ingredient can take various dosage forms such as tablet, powder, granule, sappository, capsule, alcoholic solution, oily solution and aqueous suspension. As the oily solvent, triglyceride of a fatty acid of 8 to 10 carbon atoms, corn oil, cotton seed oil, peanut oil, fish liver oil and oily ester are used. Cacao oil and glycerol are also usable. As the other component, lactose, starch, talc, magnesium stearate, sorbic acid, salts of sorbic acid, saccharides or derivatives thereof, alcohol, aqueous physiological saline solution, surfactant, antioxidant, etc. may be used together with the present substance.

The present substance may be contained in the pharmaceutical preparation in an amount of from 0.00002 to 4% by weight, preferably from 0.0002 to 1% by weight.

Further, the present substance is administered to and adult in a daily dose of 0.1 to 100,000 μg, preferably 0.5 to 10,000 μg.

The results of examination on the acute toxicity of the present substance are shown as follows. Acute toxicity:

After dissolving the present substance in ethanol, the thus formed solution was diluted by a triglyceride of a fatty acid of 8 to 10 carbon atoms so that the concentration of ethanol became 2%. The thus formed solution was orally (p.o.) administered to each of 10 male ICR mice (age of 6 weeks, body weight of 25+3 g) at dose of 150 mg/kg. On observing the presence of toxic symptoms on the animals for 2 weeks, all the animals (10 mice) survived without any abnormality. After slaughtering the test animals, the biochemical examination of the blood of the animals, the autopsy and the histopathological examination were carried out, however, no difference was found between the results for the test animals and the results for the control animals which were administered with only the triglyceride of a fatty acid of 8 to 10 carbon atoms containing 2% of ethanol. Accordingly, the acute oral LD$_{50}$ of the present substance is not less than 100 mg/kg and the present substance can be said to be extremely safe.

The present inventors examined the effect of 24,25-(OH)$_2$—D$_3$ on inhibiting the formation of urinary calculus using model animals and have found that the present substance is effective as a prophylactic for urinary calculosis.

The present invention will be more precisely explained while referring to the following non-limitative Examples. The absolute configuration of 24- position of 24, 25-(OH)$_2$—D$_3$ was identified while referring to Tetrahedron Letters No. 26, 2203 –2206, 1975.

EXAMPLE 1

As the test animals for renal calculus, the following rats were used.

Twenty male Wistar rats (age of 8 weeks and body weight of about 200 g) were allowed to take a water containing 0.5% of ethylene glycol freely, and a mixture of 0.5 μg of 1α-hydroxycholecarciferol and 0.1 ml of triglyceride of a fatty acid of 8 to 10 carbon atoms was forcibly and orally administered by a stomach tube every other day for four weeks, thereafter being used as the test animals.

24R,25-(OH)$_2$—D$_3$ in the triglyceride of a fatty acid of 8 to 10 carbon atoms containing 2% of ethanol was forcibly and orally administered to each of the test animals at a dose of 10 μg/kg/1 ml/day by a stomach tube, and to each animals of the control group, the triglyceride of a fatty acid of 8 to 10 carbon atoms was administered in the same manner as above.

The animals were slaughtered after four weeks from the first administration, and the kidney of the animal was extirpated therefrom after the exsanguination and immediately photographed by soft X-ray. Further the cross section of the extirpated kidney containing papilla was observed by naked eyes.

Results (1) Results of the observation by naked eyes:

In the control group, on the 8 cases among 10 rats, the calculi were observed in the pelvis and the papilla of the kidney, and furthermore a radial deposition of crystals was remarkably found in the renal parenchyma through the interface between the cortex and the medulla to the medulla and the papilla. However, in the group administered with 24R,25-(OH)$_2$—D$_3$ at a dose of 10 μg/kg/1 ml/day, although the radial deposition of crystals was recognized in only one rat of 10 rats, any clear calculus was never recognized.

(2) Soft X-ray photograph:

A clear inhibition of the formation of calculus was found in the rats which were administered with 24R,25-(OH)$_2$—D$_3$ as compared in the control rats.

EXAMPLE 2

After dissolving 24R,25-(OH)$_2$—D$_3$, at a prescribed concentration, into the triglyceride of a fatty acid of 8 to 10 carbon atoms containing 1 % of ethanol, the solution was forcibly and orally administered to each of the three groups of the male or female ICR mice continuously for 30 days at a daily dose of 10, 100 or 1000 μg/kg.

According to the growth curve of the thus treated animals based on the body weight, any significant difference in the body weight change was not recognized between the groups.

After fixing the following organs by an aqueous 10% solution of formalin, the thus fixed organs were stained with hematoxylin-eosin and examined histopathologically, however, any abnormal findings were not particularly recognized.

The examined organs are as follows: brain, heart, lung, liver, kidney, adrenal, spleen, pancreas, thyroid, hypothesis, thymus, mesentric lymph node, testis, ovary, uterus, stomach, small intestines (jejunum, ileum and duodenum), large intestines (colon and cecum), eyeball, submandibular gland, urinary bladder, backskin, muscle, sternum, marrow of sternum, femur and marrow of femur.

EXAMPLE 3

The triglyceride of a fatty acid of 8 to 10 carbon atoms was irradiated with ultraviolet rays from a 400W high pressure mercury lamp for 72 hours under argon bubbling to decompose the reactive peroxides contained therein as impurities. A solution was prepared by dissolving 5 mg of 24R,25-(OH)$_2$—D$_3$ into 1 kg of the thus treated triglyceride.

Soft capsule containing 0.5 μg of 24R,25-(OH)$_2$—D$_3$ in each capsule was prepared by heating and dissolving the following components for the capsular skin with a soft capsule-producing machine according to an ordinary method.

Recipe of the capsular skin based on the capsule prepared

Gelatine 10 parts by weight
Glycerol 2 parts by weight
Antiseptic (ethylparaben) 0.05 part by weight
Titan white 0.2 part by weight
Water 0 2 part by weight In the same manner, each soft capsule respectively containing 1, 2, 5 and 10 μg of 24R,25-(OH)$_2$—D$_3$ in one capsule were prepared.

What is claimed is:

1. A method for inhibiting the formation of urinary calculus, which method comprises administering a daily dose of about 0.1 to 100,000 μg of 24,25-dihydroxycholecarciferol as a pharmaceutical preparation containing said 24,25-dihydroxycholercarciferol in an amount of 0.00002 to 4% by weight.

2. A method for inhibiting the formation of urinary calculus according to claim 1, wherein said 24,25-dihydroxycholecarciferol, is 24R,25-dihydroxycholecarciferol, or a mixture thereof.

3. A method for inhibiting the formation of urinary calculus according to claim 1, wherein said 24,25-dihydroxycholecarciferol is 24R,25-dihydroxycholecarciferol.

4. The method for inhibiting the formation of urinary calculus according to claim 1, wherein the pharmaceutically effective amount is a daily dose of about 0.5 to 10,000 μg.

5. A method of prophylaxis of urinary calculosis, which comprises administering to a patient in need thereof a daily dose of about 0.1 to 100,000 μg of 24,25-dihydroxycholecarciferol as a pharmaceutical preparation containing said 24,25-dihydroxycholercarciferol in an amount of 0.00002 to 4% by weight.

6. A method for prophylaxis of urinary calculosis according to claim 5, wherein said 24,25-dihydroxycholecarciferol is 24R,25-dihydroxycholecarciferol, 24S,25-dihydroxycholecarciferol or a mixture thereof.

7. A method for prophylaxis of urinary calculosis according to claim 5, wherein said 24,25-dihydroxycholecarciferol is 24R,25-dihydroxycholecarciferol.

8. The method for prophylaxis of urinary calculosis according to claim 5, wherein the pharmaceutically effective amount ranges is a dose of about 0.5 to 10,000 μg.

* * * * *

UNITED STATES PATENT AND TRADEMARK OFFICE
CERTIFICATE OF CORRECTION

PATENT NO. : 4866047
DATED : September 12, 1989
INVENTOR(S) : Yamato, Hideyuki; Kobayashi, Yasuhiko; Kato, Tadaaki; Maeda, Yuji; Fujii, Takayoshi; Saito, Kenichi; Hirose, Fumio; Yoshikumi, Chikao It is certified that error appears in the above—identified patent and that said Letters Patent is hereby corrected as shown below:

Column 2, line 16; delete "25 + 3" and insert ---25 $\pm$ 3---.

Claim 2, line 4; before "or", insert ---24S,25-dihydrxycholecarciferol---.

Column 2, line 6; delete "and" and insert ---an---.

Signed and Sealed this

Fifth Day of March, 1991

Attest:

HARRY F. MANBECK, JR.

Attesting Officer    Commissioner of Patents and Trademarks